(12) United States Patent
Muchin et al.

(10) Patent No.: US 6,261,593 B1
(45) Date of Patent: Jul. 17, 2001

(54) CARRIER PATCH FOR THE DELIVERY OF AGENTS TO THE SKIN

(75) Inventors: Jerome D. Muchin; Michael P. Muchin, both of Los Angeles, CA (US)

(73) Assignee: Acutek International, Inglewood, CA (US)

(*) Notice: Subject to any disclaimer, the term of this patent is extended or adjusted under 35 U.S.C. 154(b) by 0 days.

(21) Appl. No.: 09/625,001

(22) Filed: Jul. 24, 2000

Related U.S. Application Data

(62) Division of application No. 09/292,625, filed on Apr. 15, 1999.

(51) Int. Cl.[7] .............................. A61F 13/00; A61F 13/02; A61K 9/00; A61K 9/14
(52) U.S. Cl. ..................... 424/443; 424/449; 424/448; 424/400; 424/484
(58) Field of Search .................................. 424/443, 449, 424/448, 400, 484

(56) References Cited

U.S. PATENT DOCUMENTS

| | | |
|---|---|---|
| 2,629,378 | 2/1953 | Barton . |
| 3,731,683 | 5/1973 | Zaffaroni . |
| 4,022,203 | 5/1977 | Ackley . |
| 4,731,926 | 3/1988 | Sibalis . |
| 4,784,857 | 11/1988 | Berry . |
| 4,812,305 | 3/1989 | Vocal . |
| 4,830,854 | 5/1989 | Copelan . |
| 5,161,688 | 11/1992 | Muchin . |
| 5,186,938 | * 2/1993 | Sablotsky . |
| 5,223,261 | 6/1993 | Nelson . |
| 5,230,898 | 7/1993 | Hortsmann . |
| 5,296,512 | 3/1994 | Beier . |
| 5,300,291 | 4/1994 | Sablotsky et al. . |
| 5,300,299 | 4/1994 | Sweet . |
| 5,350,581 | 9/1994 | Kochinke . |
| 5,370,924 | 12/1994 | Kochinke . |
| 5,468,501 | 11/1995 | Kydonieus . |
| 5,505,958 | * 4/1996 | Bello . |
| 5,512,277 | 4/1996 | Uemura et al. . |
| 5,546,929 | 8/1996 | Muchin . |
| 5,660,178 | 8/1997 | Kantner . |
| 5,702,721 | 12/1997 | Hortsmann . |
| 5,716,621 | 2/1998 | Bello . |
| 5,851,549 | 12/1998 | Svek . |
| 5,962,011 | 10/1999 | DeVillex et al. . |

* cited by examiner

Primary Examiner—Thurman K. Page
Assistant Examiner—Isis Ghali
(74) Attorney, Agent, or Firm—Oppenheimer, Wolff & Donnelly LLP

(57) ABSTRACT

A carrier patch for delivering agents locally to the skin or systemically via the skin. The patch comprises a pad having a lower surface area to which an adhesive is adhered, and a primary agent applied to discrete regions of the patch in a manner to minimize the deleterious effects of the adhesive on the primary agent. The invention further comprises a method for the discrete application of the agent to the patch, and a method of using the patch for the delivery of the agent to the skin.

25 Claims, 14 Drawing Sheets

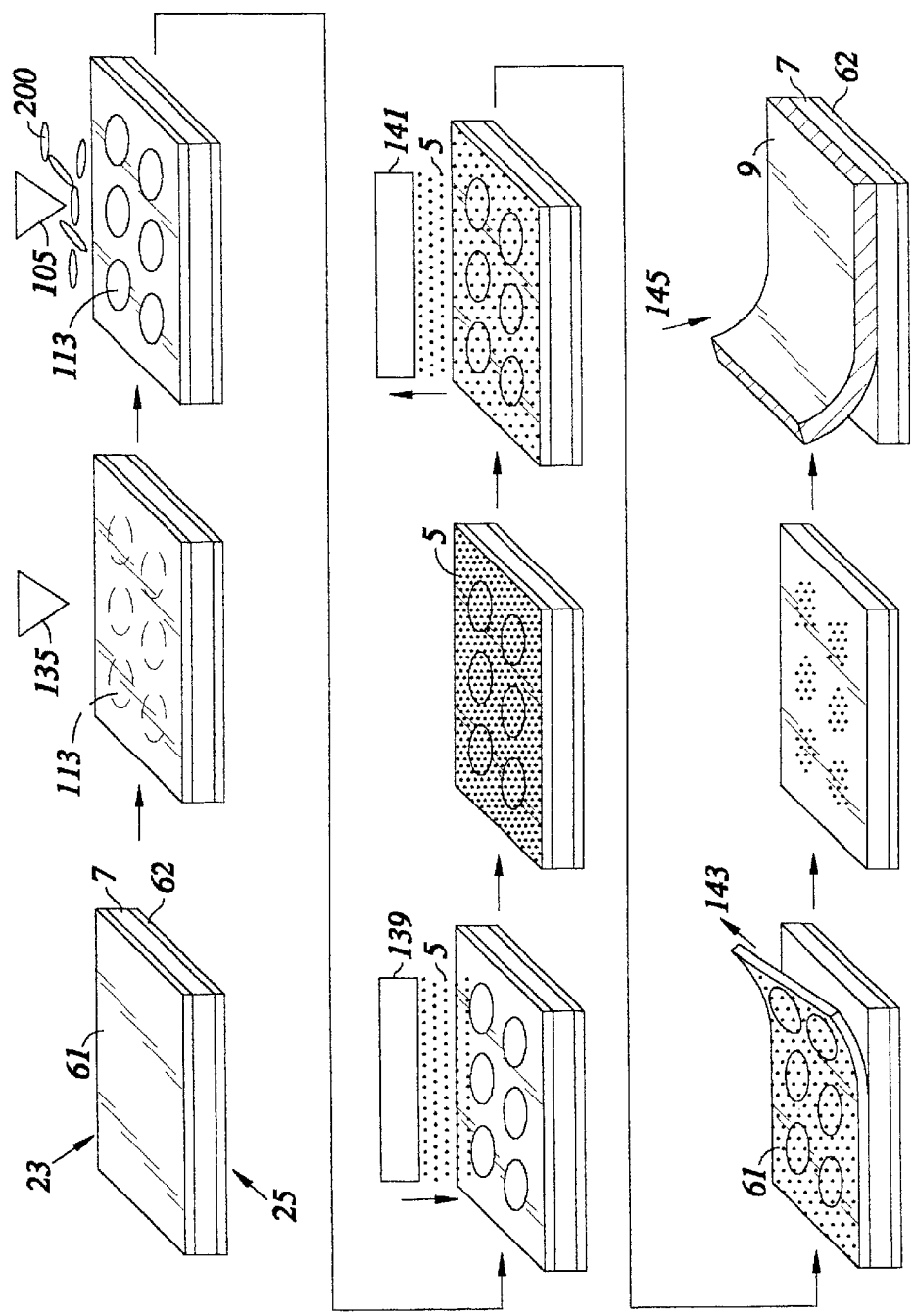

CARRIER PATCH FOR THE DELIVERY OF AGENTS TO THE SKIN

This is a Divisional of application Ser. No. 09/292,625, filed Apr. 15, 1999, which application is incorporated herein by reference.

BACKGROUND OF THE INVENTION

This invention relates to a carrier patch for the delivery of agents to the skin, a method of producing the carrier patch and a method for the use of the carrier patch. In particular, the invention is concerned with a carrier patch having an agent to be delivered to the skin, a method of applying the agent to the patch in a manner which is minimally deleterious to the agent, and a method of delivering agents to the skin using such a carrier patch.

Delivery of agents to the skin for local skin treatment may be desirable to improve the health and appearance of the skin. Skin conditions such as dry or oily skin, blemishes, abrasions, cuts or rashes, for example, require localized skin treatment to remedy the affected area and to prevent further skin damage. If skin conditions are not treated, further skin irritation may occur resulting in infections or damage to the skin. Thus, treatment of skin conditions improves the health and appearance of the skin.

Further, the skin may provide an ideal system for the delivery of agents to be active systemically. Although the skin is thought to provide the body with a protective covering, a number of agents are absorbable through the skin, and since the skin is a highly vascularized organ, the agents also penetrate into the circulating blood supply for distribution throughout the body, ultimately reaching the targets the agent is intended to affect.

Previously described methods for using patches for the local delivery of agents to the skin or systemic delivery via the skin employ a combination of the agent to be delivered with an adhesive used both to anchor the patch to the skin and as the medium by which the agent is delivered to the skin. However, the combination of the agent with the adhesive is disadvantageous for reasons including that some agents cannot be solubilized in the adhesive, the agent and adhesive when combined can each impair the effectiveness of the other, and the agent when combined with the adhesive can be heat inactivated by the thermal, chemical or mechanical actions used to cure adhesives. Thus, the combination of agent and adhesive prior to or during adhesive preparation for many agents would require a high concentration of the agent to be used in the combination such that an effective dose would remain after adhesive treatment has been completed. For some agents this is impracticable.

It is known to form sampler devices for cosmetics, wherein the device includes one or more plys. This is disclosed in U.S. Pat. No. 5,161,688 (Muchin) which is incorporated by reference herein.

There is a need to provide a carrier patch for the delivery of agents to the skin which minimizes the disadvantages of known systems.

SUMMARY OF THE INVENTION

The invention provides a carrier patch which has advantages over known systems for delivering agents to the skin. There is also provided a method for producing the patch and a method for delivering agents to the skin utilizing the carrier patch.

According to the invention, there is provided a carrier patch for delivering agents to the skin. The carrier patch has a surface area for adhering to the skin and comprises a pad, having an upper and lower surface area, and an adhesive adhered on the lower surface area of the pad. A primary agent for delivery to the skin is applied to the patch in a manner such that the deleterious effects of the adhesive on the agent are minimized. Preferably no treatment of the adhesive is necessary after applying the agent.

In some embodiments, the agent is applied directly to discrete areas of the patch pad or adhesive.

In other embodiments, the patch includes one or more liners, secured to the pad lower surface by the adhesive. In one preferred embodiment, the adhesive is used to carry the primary agent to the skin. Further, the primary agent can be applied to the adhesive in discrete locations.

Preferably, the primary agent is applied to the adhesive through apertures which are formed in a first liner, and further the first liner is selectively removable from the adhesive after applying the agent to the adhesive. The apertures in the liner effectively form a mask through which the agent is applied to the adhesive in discrete locations where the adhesive is exposed.

In some embodiments, the primary agent is applied to the lower surface of the adhesive. In other embodiments, the agent is applied to the upper surface of the adhesive.

In alternative embodiments, apertures can be formed through any portion of or the entirety of the depth of the patch material. The apertures can contain the primary agent to be delivered to the skin. In one embodiment, where the pad contains apertures, the pad remains in place after applying the primary agent to the apertures. In another embodiment, the primary agent can be applied to a surface of the pad, without forming apertures in the pad.

In some embodiments, the primary agent is applied to the patch without the use of a first liner. In some embodiments, the patch can also include a cover, secured to the pad surface to seal the pad with the agent material adhered to the adhesive.

In yet other forms of the invention the patch can be embossed such that there are indentations for receiving the agent. The adhesive may exist at only discrete locations of the patch and may be of a nature that it is at the discrete locations that the agent is applied to the patch. In such situations the use of a liner as a mask may be optional.

The primary agent to be delivered to the skin is preferably therapeutic and may be a single agent or may consist of a combination of agents applied to the patch singly or as a mixture. The pad is a substrate which is preferably flexible.

The adhesive is any substance which holds the patch in contact with the skin. Preferably the adhesive is a polymeric adhesive composition, and more preferably a pressure sensitive adhesive. Further, the adhesive is selected to have a desired property of not interfering with the action of or the delivery of the agent to the skin and has the desired property of not requiring treatment which could be deleterious to the primary agent after the primary agent is applied. In such embodiments the adhesive is effectively cured and/or in its effective operational state or condition prior to applying the agent to the patch.

In some embodiments, the patch is further active in the removal of keratotic plugs from the pores of skin. Keratotic plugs are dead epidermal cells combined with sebaceous matter and dirt which form within skin pores, and result in conspicuously enlarged and/or darkened pores. If keratotic plugs are not periodically removed from the skin, not only do pores enlarge and darken, but further skin irritation may occur resulting in reddening blemishes or bacterial infections of the skin.

In some embodiments, the patch can contain a cosmetic composition, which may conceal the underlying skin condition.

The patch may be made in a variety of shapes. At least one of and preferably both of the pad and adhesive composition may be substantially transparent or clear, a flesh-like color or shade so as to effectively blend with the skin of wearer, or translucent. In other embodiments, the pad is effectively colored or rendered ornate or patterned on its surface.

The invention also provides a method for the use of the carrier patch to deliver agents to the skin. The method generally comprises obtaining a carrier patch, removing the liner to expose a surface of adhesive with agent to the skin, applying the patch with the adhesive and agent to the skin with the lower surface of the pad adhering to the skin through the adhesive, and subsequently removing the patch from the skin.

The invention also provides a method for producing the patch which generally comprises providing a material comprising a pad and an adhesive, the adhesive being in an effective operational state. Apertures are formed in relation to the patch thereby forming a mask effect such that discrete areas of adhesive are exposed and a primary agent is applied to the patch to adhere to the exposed adhesive. Excess primary agent is removed from the surface of the patch, and the patch, with adhered adhesive can be further processed or prepared for subsequent use.

The invention is further described with reference to the accompanying drawings.

DESCRIPTION OF THE DRAWINGS

FIG. 5e is a diagrammatic view of the patch at various stages during a fourth method of manufacture.

DETAILED DESCRIPTION OF THE PREFERRED EMBODIMENT

Figure 1A:
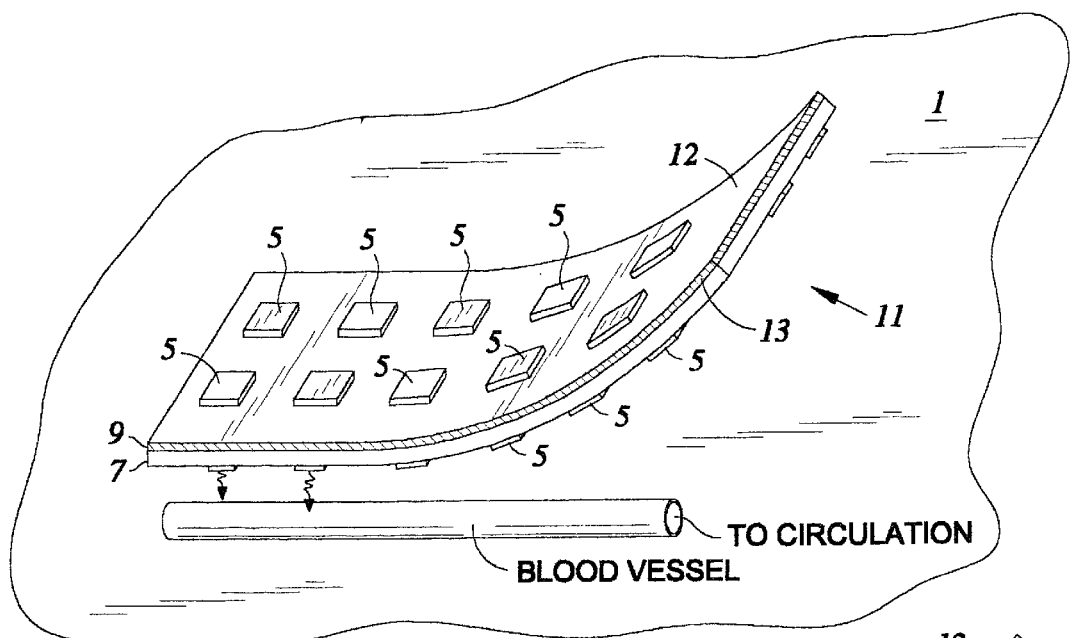
FIG. 1a is a perspective view of the patch being applied to the skin with primary agent adhered to the adhesive on the lower surface area of the pad.

A carrier patch 11 delivers an agent 5 upon application of the patch 11 to the skin 1 of a user (FIG. 1a). In FIG. 1a there is shown a pad 9 without apertures, and adhered to the underside of the pad 9 is an adhesive 7 to which is adhered at discrete locations the agent 5. The agent 5 had been applied to the adhesive 7 through a mask technique as described further below, and at a time when any further treatment, if any, of the adhesive 7 was of a nature that it would not deleteriously affect the efficacy of the agent 5. The mask technique and pad 9 without apertures 113 is a particularly preferred technique for creating the invented patch. This embodiment is further illustrated in FIG. 2a.

Carrier Patch Pad

The patch 11 includes a pad 9 having an upper surface area 12 and a lower surface area 13 and a peripheral edge 15; an adhesive 7 on the lower surface area 13 of the pad 9, and an agent 5 for delivery to the skin 1 of a user or patient.

The pad material which is useful for this invention is not particularly limited as long as it can provide a suitable substrate for the adhesive and is sufficiently strong to withstand removal from the skin, having been secured to the skin by adhesive. In some embodiments, the pad should provide a suitable substrate for the formation of apertures therein.

Figure 1B:
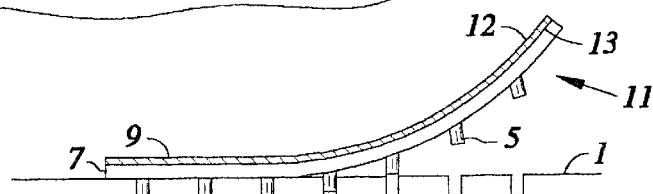
FIG. 1b is a side view of the patch being removed from the skin with adhered keratotic plugs.
Figure 1C:
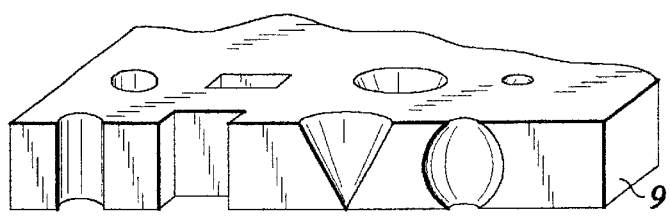
FIG. 1c is an exploded cross-sectional view of various shapes of apertures in the patch.
Figure 1D:
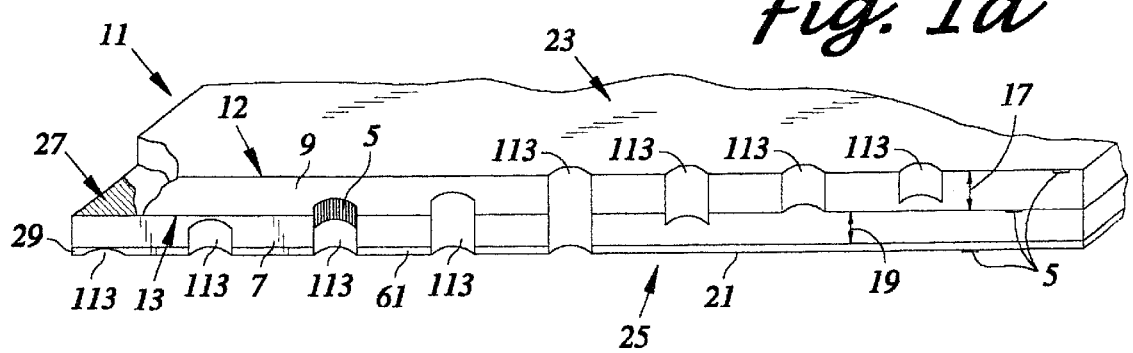
FIG. 1d is an exploded cross-sectional view of various depths of apertures in the patch, and with part of the pad broken away.

The pad 9 defines a depth 17, and the adhesive 7 defines a depth 19 (FIG. 1d). In some alternative embodiments, apertures 113 can be provided in the patch 11. These apertures 113 can be formed through a portion of or the entirety of the depth 17 of the pad and/or the depth 19 of the adhesive. The apertures 113 can contain the agent 5 to be delivered to the skin. Different cross-sections for the apertures 113 are possible in any one or more areas of the patch 11. Exemplary cross-sections are shown in FIG. 1e. Any one patch 11 would preferably have the same cross-sectioned shape of aperture 113 throughout.

Alternatively, the pad 9 and/or adhesive 7 may be of a material which is embossed, punched or otherwise configured to form a cavity therein, without the need to make a hole or aperture through the pad 9 and/or adhesive 7.

Figure 2A:
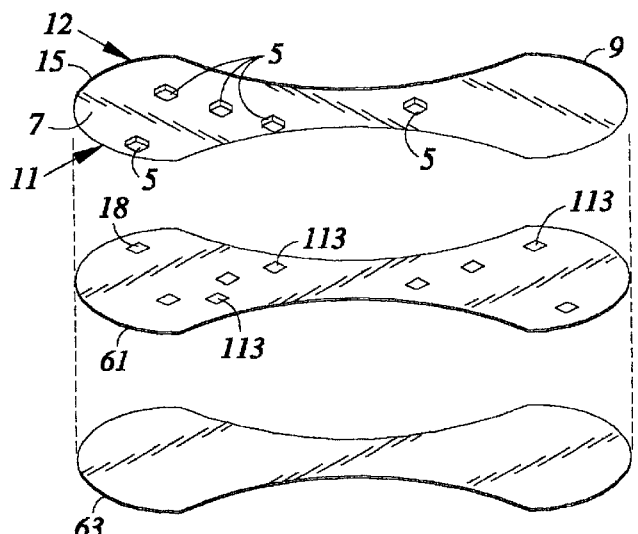
FIG. 2a is an exploded perspective top view of a first embodiment of components making up the patch. The pad has no apertures, and the liner has apertures for applying the agent to the adhesive. A protective liner is also illustrated.
Figure 2B:
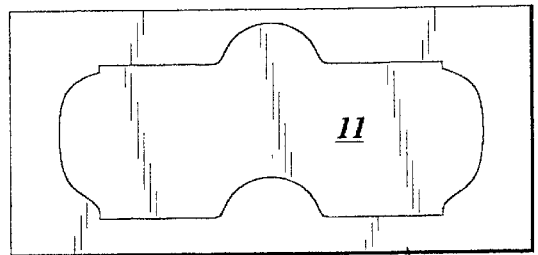
FIG. 2b is a top view of a second embodiment of components making up the patch.
Figure 2C:
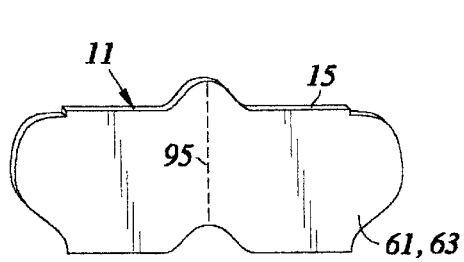
FIG. 2c is an exploded perspective bottom view of a third embodiment of components making up the patch.
Figure 2D:
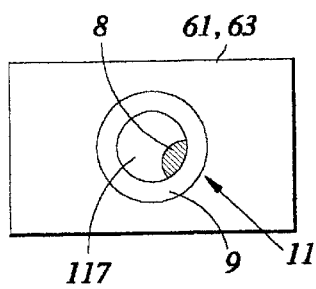
FIG. 2d is a top view of a fourth embodiment of components making up patch, and having a portion broken away.
Figure 4A:
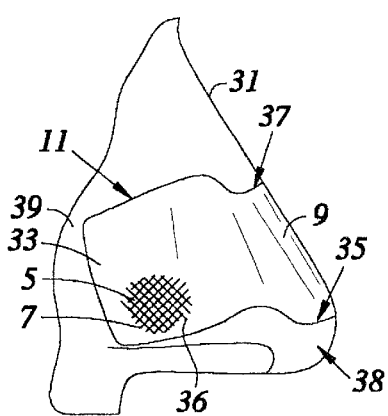
FIG. 4a is a side view of an elongated, curvilinear rectangle-like shaped patch on the skin of the nose.
Figure 4B:
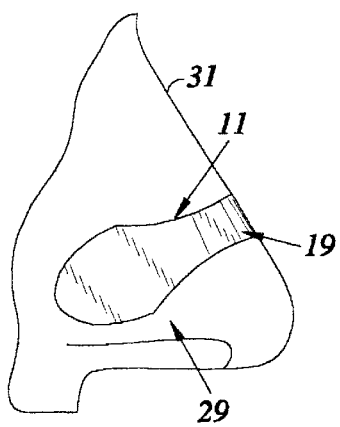
FIG. 4b is a side view of an hour-glass shaped patch on the skin of the nose.
Figure 4C:
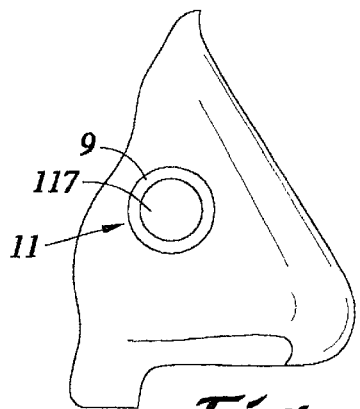
FIG. 4c is a side view of round shaped patch on the skin of the nose.

In some embodiments, the patch can include a cover 117, secured to the pad upper surface to seal the pad with the agent material (FIG. 4c). The cover may be formed of a clear plastic material, such as mylar, for example. Further, the cover may be adhered to the pad upper surface by an adhesive layer 8. In FIG. 2d a portion of the cover 117 is broken away so that the adhesive layer 8 between the pad 9 and the cover 117 is shown.

The pad material is preferably flexible from the viewpoint of comfort. The flexibility is achievable by elasticity in any one or all axes of the material. Examples of flexible materials include, but are not limited to cotton cloth, rayon cloth, tetron cloth, nylon cloth or plastic foam. The pad material is preferably pliable to accommodate skin contours, when applied to areas of skin having alterations in surface angles (for example around the nostril skin area). The pad is preferably non-stretchable, namely non-elastic, in the planar axis of the material. This is the plane defined between the upper surface 12 and lower surface 13.

The pad material is also preferably breathable, thereby allowing air to pass through the patch and contact the skin. In some embodiments, however, the pad may not breathable. The pad material is also preferably not permeable to the agent applied to the patch. However, in some embodiments it is preferable that the pad be permeable to the agent.

The pad material is also preferably of a thickness to provide sufficient strength to the pad, but also of a thinness which will be comfortable to the wearer and pliable to contact all skin surfaces. The approximate thickness can vary between the range of, but is not limited to, about 0.01 mm to about 0.05 mm.

The pad is preferably not of a woven material, and preferably has a primarily uniform surface. Where the pad is of a woven material, the material can be woven to achieve a variety of woven patterns on the surface. Examples of woven patterns, include, but are not limited to a squares, circles or diamonds on the upper and/or lower surface of the pad. Such woven patterns may result in either pad surface being primarily uniform or textured 36 (FIG. 4a). Such texture may provide an enhanced substrate for the adherence of the adhesive to the pad, as well as improved effectiveness for delivery of agents to the skin or removal of keratotic plugs from the skin. The pad is preferably non-microporous.

When the pad material is microporous, the microporous film can be, but is not limited to, an open-celled microporous film which is a microporous polypropylene such as CEL-GRAD™ (Celanese Fibers Marketing Company). Other such materials can be substituted provided they posses similar necessary qualities: namely open-celled, microporous materials that are essentially hydrophobic. Suitable examples include, but are not limited to, nonwoven materials comprising fibers selected from the group consisting of polyester, polyether and polyolefin fibers or nonwoven pulp sheets impregnated with polyethelene.

Pad materials which are not flexible may take the form of plastic film sheets, for example as described in U.S. Pat. No. 5,512,277 (Uemura).

Adhesive

The patch 11 includes the pad 9 having a lower surface area 13 covered by an adhesive 7. The adhesive 7 is located on the lower surface of the pad 13 and the adhesive has an upper surface 27 and a lower surface 29. In some cases, the adhesive 7 can be located on the entirety of the lower surface 13 such that the entire engaging surface of the pad 9 wholly adheres with the skin 1 of a user. In other cases, the adhesive 7 is not located on the entirety of the pad lower surface area 13. There could be spaces or blank areas in the pad 9 lower surface 13 which has no adhesive 7. This could facilitate delivery of the agent 5 to the skin 1 or removal of the patch 11 from the skin 1. The blank areas could be located at any suitable strategic location on the pad lower surface 13.

An adhesive useful in this invention is any substance which holds the patch in contact with the skin. In the preferred embodiment, the adhesive 7 is used to carry the primary agent 5 to the skin. Following the application of the primary agent 5 to the patch 11, the adhesive 7 does not require subsequent treatment which could be deleterious to the primary agent 5. Examples of treatments which may be deleterious include, but are not limited to, curing of the adhesive 7 by thermal, chemical or mechanical action or any other processing of the adhesive 7 involving thermal, chemical or mechanical action.

In some embodiments, where blanks areas (areas devoid of adhesive) are located on the pad lower surface, agent may be applied to the pad directly with or without the use of a liner.

In some embodiments, the primary agent 5 is applied to the lower surface 29 of the adhesive 7. In other embodiments the primary agent 5 is applied to the upper surface 27 of the adhesive.

In some embodiments, the agent may be applied to discrete areas of adhesive without the use of a liner.

Figure 5A:
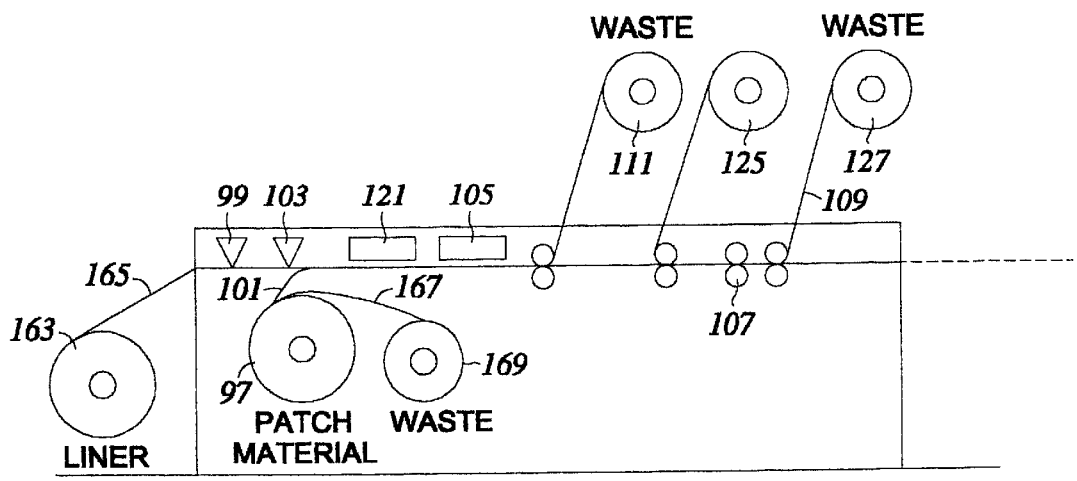
FIG. 5a is a diagrammatic view of a construction procedure for manufacturing the patch.
Figure 5B:
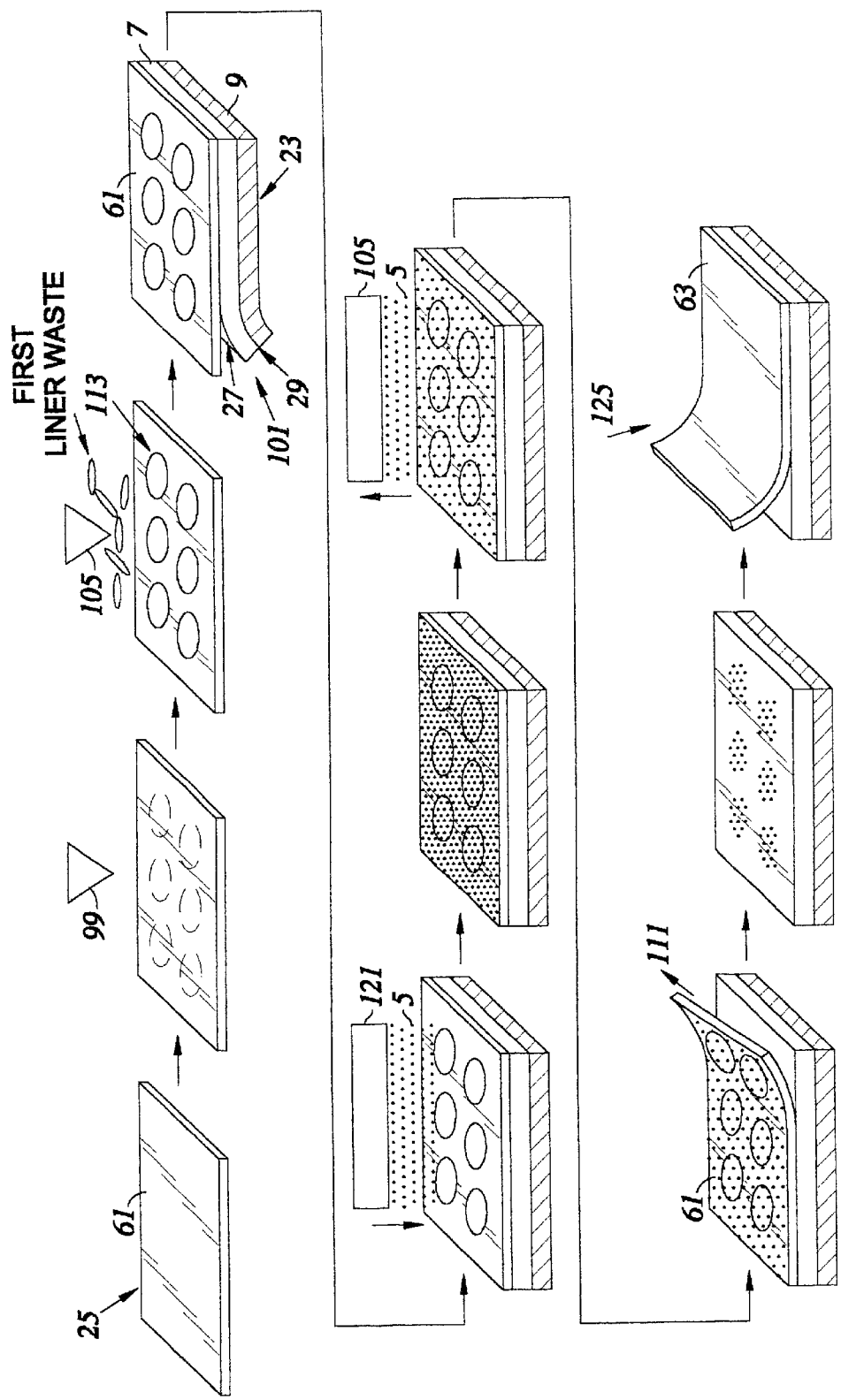
FIG. 5b is a diagrammatic view of the patch at various stages during one method of manufacture.

In the preferred embodiments, the primary agent 5 is applied to the adhesive 7 through apertures 113 which are formed in a first liner 61, exposing discrete areas of adhesive 7 (FIGS. 5b & 5e). When the liner 61 and primary agent 5 are applied to the lower surface 29 of the adhesive 7, and the primary agent 5 adheres effectively to the adhesive. The first liner 61 is then removed and a second liner 63 can be applied to cover the adhesive 7 and agent 5 until the patch 11 is to be applied to the skin 1 (FIG. 5b). When the liner 61 and primary agent 5 are applied to the upper surface 27 of the adhesive 7, and the primary agent 5 adheres effectively to the adhesive 7, the first liner 61 is removed and a pad 9 can be applied to cover the adhesive and agent (FIG. 5e).

The adhesive defines a depth 19 (FIG. 1d). In alternative embodiments, apertures 113 can be formed through a portion of or the entirety of the depth 19 of the adhesive 7. The apertures 113 can contain the agent 5 to be delivered to the skin 1.

The adhesive 7 is preferably efficient at adhering to the skin, but not damaging to the skin 1. The adhesive 7 further preferably has a relatively greater adherence to the pad 9 than to the skin 1. There can be a desired range of adhesive strength for the adhesive 7 in the present invention. The strength can vary relative to the selected pad material.

In some embodiments, the adhesive 7 is further efficient in removing keratotic plugs from the pores of the skin 1. Where the patch 11 is used not only for the delivery of an primary agent 5 to the skin, but to remove keratotic plugs from the skin 1, the strength of adhesion between the skin and adhesive is preferably maximally efficient at removing keratotic plugs from the pores of skin, while adhesion is not so aggressive as to damage skin upon the removal of the patch.

The thickness or depth 19 of the adhesive layer 7 is preferably thick enough to afford suitable adhesion between the patch 11 and the skin 1 of the user. The approximate thickness can vary between, but is not limited to the range of, about 0.01 mm to about 0.05 mm. Where more adhesive 7 is applied, the strength of the adhesive will be less.

As will be appreciated, the adhesive 7 should be applied to the pad 9 in such a manner as to provide as uniform a coating as possible. While coating weights may vary widely, depending on the adhesive used, for example between about 15 gm and about 60 gm per square meter, coating weights of between about 15 gm and about 30 gm per square meter are preferred.

The adhesive material 7 which is useful for this invention is not particularly limited as long as it can provide suitable adhesion to the skin, and is not deleterious to the activity or delivery of the primary agent 5. The adhesive 7 can be rubber, acrylic or silicone based, for example.

In some embodiments, the adhesive may be a hydrocolloid or hydrogel.

The adhesive 7 is preferably a polymeric adhesive composition. In one preferred embodiment, the polymeric adhesive composition comprises a pressure sensitive polymer. An example of a pressure sensitive polymer is, but is not limited to an acrylate adhesive. The adhesive can be selected to have a desired property of being in an active form once adhered to the pad, such that the adhesive need not be premoisturized by the user prior to application to the skin to effect its operation. The adhesive, further, preferably can include less than about 59% by weight of the composition of solvent, and most preferably includes less than about 29% by weight of the composition of solvent.

Alternatively, the adhesive 7 can be selected to have a desired property of requiring premoisturization by the user prior to application to the skin to effect its operation. Examples of adhesives which require premoisturization prior to application are, but are not limited to, those described in U.S. Pat. No. 5,512,277 (Uemura) incorporated herein by reference.

In one embodiment, the adhesive can consist of essentially of high-molecular weight polymers. Examples of high-molecular weight polymers which are useful in the invention include, but are not limited to, the homopolymers and interpolymers derived from monomers selected from the $C_2$ to $C_{10}$ aliphatic esters of acrylic and methacrylic acid, $C_2$ to $C_{10}$ aliphatic vinyl ethers and esters, acrylamides, urethanes and the like. For example, a terpolymer of 2-ethylehexyl acrylate, vinyl acetate and tert-butyl acrylamide can be particularly suitable. One such suitable terpolymer has the foregoing monomeric components present in approximate ratios of 60:25:15.

The efficacy of the adhesive 7 can be enhanced when a pigment is further incorporated together with the mentioned polymers. The pigment is not particularly limited, and both organic and inorganic pigments can be used. Examples of the inorganic pigments are, but are not limited to, zinc oxide, titanium oxide, silica, alumina, barium sulfate, zirconium oxide, calcium carbonate, calcium silicate, ceramics, hydroxyapatite, boron nitride, sericite, mica, talc, kaolin, montinorillonite, hectorite, saponite, black iron oxide, yellow iron oxide, red iron oxide, prussian blue, ultramarine, carbon black, pearlescent pigments. Examples of the organic pigments are, but are not limited to, silk powders, cellulose powders, poly(meth)acrylic ester resins, polyamide resins, polyolefin resins, polyimide resins, polyurethane resins, polyester resins, polyether resins, polyvinyl chloride resins, urea resins, polyformaldehyde resins, polycarbonate resins, polyvinylacetate resins, polyvinylidene chloride resins, polyacrylonitrile resins, polysulfone resins, polystyrene resins, polyurea resins, silicone resins, melamine resins, polytetrafluoroethylene resins, rake pigments and azo dyes.

The particle size of the pigments is from about 0.001 to 1000 micrometers, and preferably from about 0.01 to 500 micrometers. Particle size of less than 0.001 micrometer is not preferred because good dispersibility cannot be obtained. Particle size over 1000 micrometers is not preferred, either, because of an unfavorable sensation to the skin. The mentioned pigments can be used as a complex or a mixture of one or more, if desired. The amount of the pigment is from about 0.1 to 70% by weight, preferably from about 1 to 40% by weight based on the total weight of the preparation.

The efficacy of the adhesive can also be enhanced when an oil component is incorporated. This is because the strength of the film at which it breaks upon peeling-off can be controlled by the oil component. The oil component which is useful in this invention is a glycerol derivative represented by formula (1):

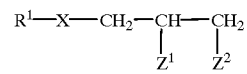

(I) wherein one of $Z^1$ and $Z^2$ represents $R^2$—Y— and the other represents a hydroxyl group or $R^3$—Y—, and $R^1$, $R^2$ and $R^3$ independently represent a hydrocarbon group, the total carbon number of which ranges from 13 to 40, and the hydrocarbon group may or may not be substituted by a silicone residual group, X and Y independently represent an oxygen atom or a group —COO—, (a carboxyl group in which the C atom is bonded to $R^1$, $R^2$, or $R^3$). Other oily ingredients which are generally incorporated into cosmetic preparations can also be used. Examples of the oil components which are useful in this invention include, but are not limited to, vegetable oils such as avocado oil, tsubaki oil, macadamia nut oil, olive oil and jojoba oil; animal oils and fats such as beef tallow, lard and egg yolk fat; aliphatic acids such as oleic acid and isostearic acid; alcohols such as hexadecyl alcohol and oleyl alcohol; esters such as cetyl 2-ethylhexanoate, 2-ethylhexyl palmitate, 2-octyldodecyl myristate, neopentyl glycol di-2-ethyl hexanoate, 2-octyldodecyl oleate, isopropyl myristate, glycerol triisostearate, mono-2-ethylhexanoic glyceryl diparamethoxycinnamate; and hydrocarbons such as dimethylpolysiloxane, dimethyl cyclopolysiloxane, methylphenyl polysiloxane, methylhydrogen polysiloxane, octamethyl cyclotetrasiloxane, octamethyl cyclopentasiloxane, decamethylcyclopentasiloxane, liquid paraffin, squalane, vaseline and solid paraffin.

Among these oil components, glycerol derivatives of formula (1) which are liquid at 20° C. are preferred, and particularly, tri-2-ethylhexanoic glycerol, 1-isostearoyl-3-myristoyl glycerol, 2-ethylhexanoic diglyceride, 1-hexyl-3-undecamethylhexasiloxy propynyl glycerol are most preferred.

The amount of the oil components to be incorporated into the adhesive of this invention is from about 0.5 to 30% by weight, preferably, about 1 to 15% by weight based on the total weight of composition.

The adhesive 7 can further contain optional ingredients which are generally incorporated into cosmetic preparations. Examples of such optional ingredients include, but are not limited to, ethylene glycol, diethylene glycol, triethylene glycol and higher polyethylene glycols; propylene glycol, dipropylene glycol and higher polypropylene glycols, 1,3-butylene glycol, 1,4-butylene glycol and other butylene glycols; glycerol, diglycerol and higher polyglycerols; sugar alcohols such as sorbitol, mannitol, xylitol and maltitol; ethylene oxides (hereinafter referred to as EO) such as glycerols; addition products of propylene oxide (hereinafter referred to as PO); EO or PO adducts of sugaralcohols; monosaccharides such as galactose, glucose and fructose, and their EO or PO adducts; polysaccharides such as maltose and lactose, and their EO or PO adducts (polyols); surfactants such as POE alkyl ethers (POE is polyoxyethylene), POE branched alkyl ethers, POE sorbitan esters, POE glycerol fatty acid esters, POE hydrogenated castor oil, sorbitan ester, glycerol fatty acid esters and polyglycerol fatty acid ester; drugs such as vitamins, antiphlogistics, activators, UV absorbers and the like; water-swelling clay minerals such as montmorillonite, saponite and hectorite; polysaccharides such as carageenan, xanthangum, sodium alginate, pullulan, methylcellulose, carboxymethylcellulose, hydroxyethylcellulose and hydroxypropylcellulose; synthetic polymers such as carboxyvinyl polymers, polyvinyl pyrrolidones and polyvinyl alcohols. They are incorporated into the adhesive in such amounts that will not impede the effects of the adhesive or agent. In particular, when polyols are used, they are preferably incorporated by in about 0.01 to 50% by weight based on the total preparation.

Agents

The patch 11 can contain any one or a combination of any number of component agents 5 to form the primary agent to be delivered to the skin. Component agents may be mixed together prior to application to the patch, or each component agent may be applied to the patch independently. Each component agent of the primary agent 5 may be directed toward the treatment of the same condition, or component agents of the primary agent may be directed toward the treatment of different conditions. The primary agent is preferably therapeutic. The primary agent can be selected to have the desired property of not interfering with the effectiveness of the adhesive of the patch. Also, the agent and adhesive are such that the adhesive does not effect the operative nature of the agent. As such the agent is preferably applied to the adhesive in a manner such that if any further treatment of the adhesive is necessary it does not impair the effectiveness of the agent.

In the preferred embodiment, the agent can be applied to the patch in discrete locations. In some embodiments, the agent 5 is applied to the upper surface 2 or lower surface 29 of the adhesive 7 of the patch 11, or both surfaces, through apertures which are formed in a liner to expose discrete regions of adhesive 7 (FIGS. 5b & 5e). In an alternate embodiment, the agent 5 is applied to the adhesive 7 without the use of a liner.

In alternative embodiments, the primary agent 5 can be applied to apertures 113 formed in discrete locations through any portion of or the entirety of the depth of the adhesive 7, the pad 9 or the liner 61 (FIG. 1d).

The primary agent can comprise skin enhancing agents. Examples of skin enhancing agents include, but are not limited to, antiseptics, such as alcohol, peroxide or betadine; antimicrobials; antibacterials, such as Triclosan, or Polysporin™; anti-virals, such as Nonoxyl-9; antifungal agents, such as imidazole; wound healing promoters; sunscreens; moisturizers, such as aloe or vitamins A, D or E; detoxifiers and degreasers, such as witchazel, camphor and acetone; wrinkle reducers, such as salicylic acid, tocopherol, N-acetyl-L-cystine and its derivatives; or pharmacologically active agents, including, but not limited to, analgesics, anesthetics, anti-inflammatories, steroids, nicotine, anti-acne medications, appetite stimulators or suppressants, retinoids, benzoyl peroxide or salicylic acid.

The primary agent 5 can also comprise a skin reduction agent. Examples of skin reduction agents are, but are not limited to, anti-wart medications, such as dinitrochlorobenzene, diphenylcyclopropenone, squaric acid butyl ester, propolis and cyclohexamide; anti-scaring medications such as cortisone; and exfolient enhancers, such as alpha-hydroxy acid.

The primary agent 5 can also comprise a cosmetic agent. The cosmetic can be in various physical forms such as liquid, including cremes and lotions, as well as powders.

The primary agent 5 can also comprise component agents which aid in the activity or absorption of other component agents. Examples of such component agents are, but are not limited to percutaneous penetration enhancers, such as surfactants, lipophilic solvents, hydrophilic solvents (alcohol, fatty acid esters) DMSO, carboxylic acids, propylene glycol, sodium methyl cocoyl taurate or sodium methyl oleoyl taurate; dyes; preservatives or stabilizers.

Figure 5C:
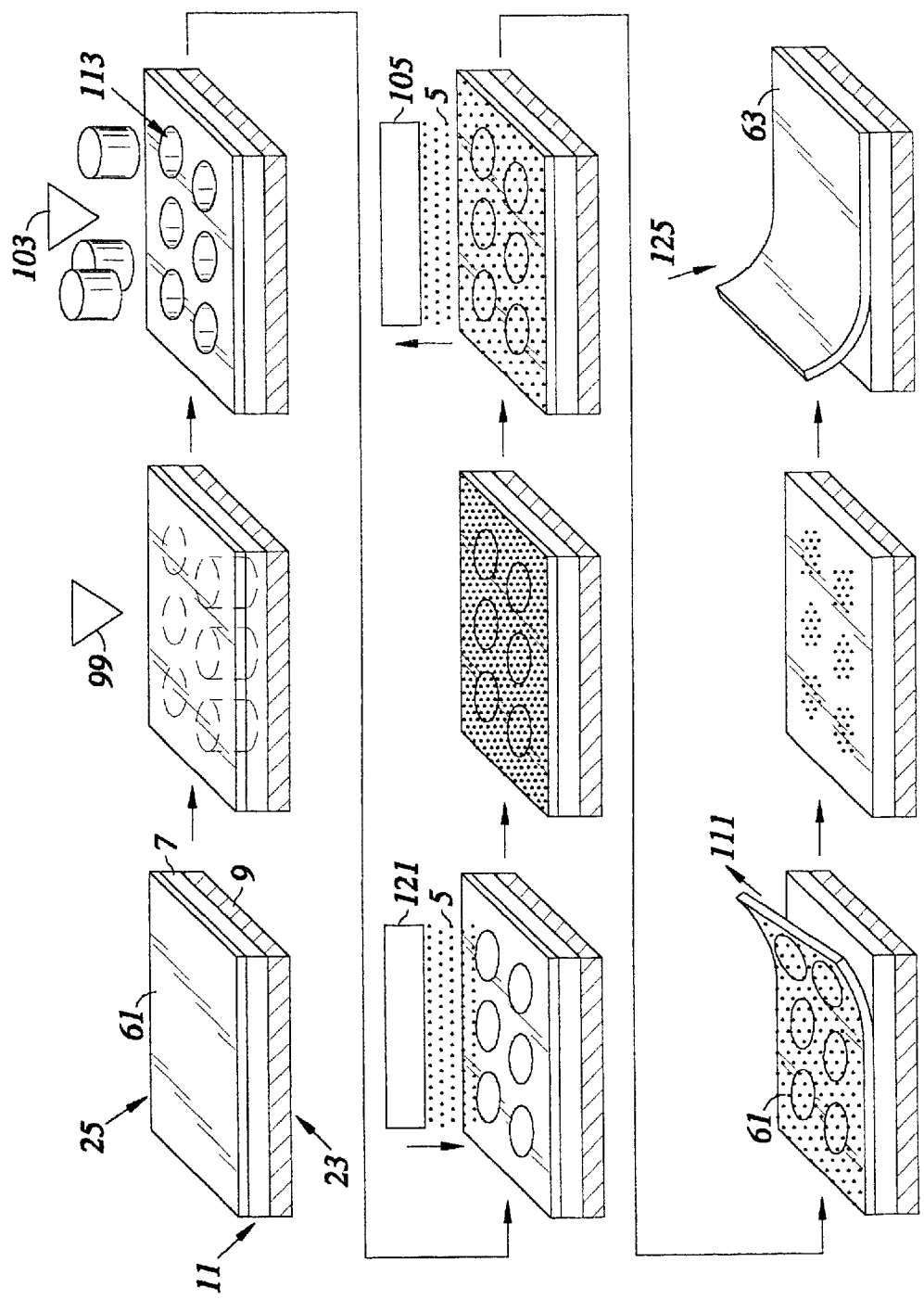
FIG. 5c is a diagrammatic view of the patch at various stages during a second method of manufacture.
Figure 5D:
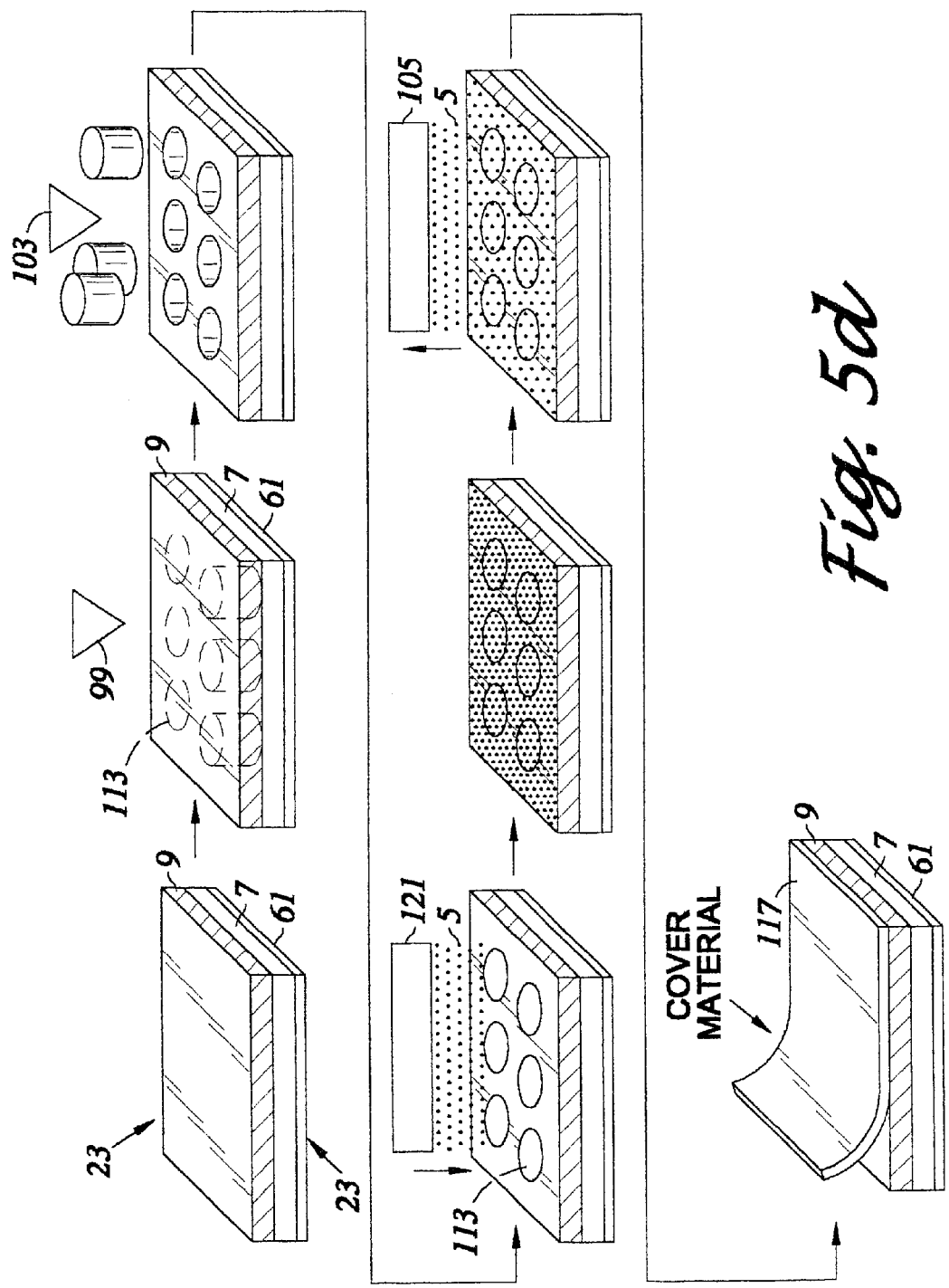
FIG. 5d is a diagrammatic view of the patch at various stages during a third method of manufacture.

The primary agent 5 can be in any variety of physical forms, including but not limited to a solid, such as a powder, liquid or a combination thereof, such as a creme, gel or ointment (including, but not limited to a petroleum jelly based ointment containing active agents (such as polymyxin B sulfate and/or bacitracin zinc-neomycin sulfate) or a hydrocortizone ointment, for example). The primary agent can also be microencapsulated or aerosolized prior to application to the patch.

Where the agent 5 is a liquid or semi-liquid, the primary agent may require evaporation of a volatile solvent from the primary agent prior to completion of the manufacture process. In some embodiments, particularly where the primary agent is a volatile liquid or only a small amount is desired, the primary agent is first absorbed onto an absorbent material 65, such as a die cut sponge, paper, cloth or molecular sieve and the absorbent material then placed into the aperture. Once the sample is exposed, there is a controlled transpiration of the primary agent. Such embodiments can also include a perforated ply 67 over the opening of the aperture(s) on the lower surface of the patch to allow exposure or evaporation of the sample without direct contact of the sample with the skin. The amount of exposure or rate of evaporation can be regulated by the size and number of perforations (FIG. 5g). In some embodiments, the perforations can be made throughout the entirety of the surface area of the ply, or perforations can be made in discrete areas of the ply. In further embodiment, the perforated ply may have a pressure sensitive adhesive on its lower surface, so as to adhere the patch to the skin surface. Further, the adhesive may have adhered thereto a liner.

The primary agent 5 is preferably present in an amount and a concentration such that an effective dose of the agent will be applied to the skin over the designated time that the patch remains adhered to the skin. The dosage of agent available to the skin may be altered by altering the density of the discrete applications of the primary agent to the defined surface area of the patch, the cross-sectional area of each application for a defined surface area of the patch, the cavity volume (as measured by the depth and cross-sectional area) of the aperture containing the agent in a defined surface area of the patch, or any combination of these parameters described. Thus, where a liner is used as a mask in adding agent to the patch, the greater the depth of the apertures in the liner, the greater the amount of agent available for delivery to the skin. Similarly, the greater the density of apertures, or the cross sectional area of the apertures, the greater the amount of agent available for delivery to the skin.

Delivery of the primary agent to the skin may proceed by a process including, but not limited to, liquefaction upon moisturization of the agent, diffusion of the agent away from the patch or capillary action of the agent from the patch to the skin.

In further embodiments the agent can also include secondary agents to be applied to the patch pad, adhesive or both. Each secondary agent may be directed toward the treatment of the same condition or different conditions than the primary agent. Alternatively, secondary agents may not serve in the treatment of a condition at all. Secondary agents can improve the attractiveness of the patch for marketing to a particular group of consumers, enhance the setting in which it is used, for example a spa environment, or enhance the ultimate goal of skin care by providing additional substances which are beneficial to the skin. Examples of secondary agents include, but are not limited to fragrances or additional skin enhancers. Fragrances can be, but are not limited to men's or women's perfumes or plant extracts, such as fruit, floral or herbal scents.

In yet further situations the agent can be a therapeutic product for absorption within the blood vessels and blood stream of a user to be circulated and to affect the physiology of the user. In yet other cases the agent may be for use as a part of a diagnostic product for a patient.

Agent Application

In some embodiments, where blanks areas (areas devoid of adhesive) are located on the pad lower surface, agent may be applied to the pad directly with or without the use of a liner.

In other embodiments, agent may be applied to the adhesive directly without the use of a liner.

In one preferred embodiment, the adhesive 7 is used to carry the agent 5 to the skin 1. The primary agent 5 can be applied to the lower surface 29 of the adhesive or the upper surface 27 of the adhesive. In other embodiments, the primary agent can be applied to both the upper and lower surfaces of the adhesive.

Preferably, the agent 5 is applied to the adhesive 7 through apertures 113 which are formed in the first liner 61 (FIGS. 5b & 5e). When the liner and agent 5 are applied to the lower surface area 29 of the adhesive, and the primary agent adheres effectively to the adhesive 7 by engaging the adhesive in the areas of the apertures 113. The first liner 61 is then removed. A second liner 63 can be applied to cover the adhesive 7 and the adhered agent 5 until the patch 11 is to be applied to the skin 1. When the liner 61 and agent 5 are applied to the upper surface area 27 of the adhesive 7, and the agent adheres in the area of the apertures 113 effectively to the adhesive 7. The first liner 61 is then removed, and a pad 9 is applied to the adhesive 7.

In another alternative embodiment, the agent 5 can be added to the pad surface without forming apertures in the pad 9. Where the agent 5 is applied to the upper side of the patch 23, the agent 5 can be added to the pad surface 12, and a cover 117 added to the upper surface 12 of the pad 9, so as to seal the pad 9 with the agent 5. An adhesive 8 is used between the cover 117 and surface 12.

In an alternative embodiment, the agent 5 can be delivered to discrete locations of the patch by formation of apertures 113 for containing the agent 5 to be delivered to the skin. The depth of the apertures 113 can extend through any portion or the entirety of the pad 9, adhesive 7 and/or liner 61 (FIG. 1d). Examples of the depth to which the aperture can extend include, but are not limited to, the liner only (when present), the adhesive only, the pad only, the liner and the adhesive, the adhesive and pad, or all of the liner, adhesive and pad.

Where the agent is applied to the lower side 25 of the patch 11, a first liner 61 may be used on the adhesive 7. The apertures 113 can extend into the adhesive 7 and/or pad 9 (FIGS. 5b and 5c). After the agent 5 is applied to the apertures 113, the first liner 61 is removed and a second liner 63 can be applied to cover the adhesive 7 and agent 5 until the patch 11 is to be applied to the skin 1. Where the agent 5 is applied to the upper side 23 of the patch 11, the agent 5 can be added to the apertures 113, and a cover 117 added to the upper surface 12 of the pad 9, so as to seal the pad with the agent.

The three dimensional shape of the apertures 113 in the pad 9 and/or adhesive 7 is not particularly limited as long as it can provide a suitable reservoir for the agent 5 to be delivered to the skin 1. Examples of the three-dimensional shapes the apertures can be include, but are not limited to, cylindrical, conical, pyramidal, spherical or cubical (FIG. 1c), as shown in the depth of the pad 9 for example. Further, apertures can be isolated shapes, or may be continuous in the form of channels, running parallel, or anti-parallel in the planar direction of the patch materials.

The density of the discrete applications of the agent 5 to the patch is not particularly limited as long as the remaining patch materials are suitably effective in adhering to the skin 1 and suitably strong to withstand the removal of the patch from the skin having been attached to the skin by the adhesive. In some embodiments, the agent can be located on about 100% of the surface area of the patch 11. Preferably, the density of discrete applications of agent 5 to the patch 11 is less than about 75% of the surface area of the patch 11. More preferably it is less than about 50% of the surface area of the patch, and most preferably it is less than about 25% of the surface area of the patch 11.

A particular patch 11 can have a variety of shapes and densities of the discrete applications of the agent 5 to the patch, and when selected a variety of depths of apertures, as well.

In some embodiments, after the agent is applied to the patch, the agent may be treated to improve its effectiveness.

Liner

In some embodiments, the patch 11 includes a liner 61 to aid in the application of the agent 5 to the patch to the adhesive 7 prior to use. In some embodiment, the first liner 61 is located on the lower surface area of the pad 13, such that the entire engaging surface adhesive is covered from exposure during manufacture of the patch, and a second liner. In some embodiment, the first liner 61 is located on the lower surface area of the pad 13, such that the entire engaging surface adhesive is covered from exposure prior to use of the patch (FIG. 2a).

The liner 61 is shown with apertures 113 through which the agent 5 is applied to the adhesive 7. There can also be a liner 62 without apertures used to protect the adhesive 8 prior to use. A liner 63 without apertures can be applied to the adhesive containing agent 5 after application of the agent 5 and subsequent removal of the liner 61.

The liners 61, 62 and/or 63 are also preferably designed to facilitate removal of the liner from the pad by a user or during manufacture. Preferably the composition of the liner is such that any agent contained on the pad has a greater affinity for the patch adhesive and/or pad than the liner.

Examples of suitable liner materials include, but are not limited to bleached Kraft-Glassine paper, silicone coated on both sides, mylar or polyethylene.

The liner 61 is preferably designed to withstand the formation of apertures therein for the formation of a mask. The thickness of the liner is not particularly limited. The approximate thickness can vary between the range of, but is not limited to about 1 mm to about 20 mm.

The liner can be of the same dimensions as the pad, or may be of different dimensions than the pad to facilitate removal of the liner from the pad. Where the liner is of different dimensions as the pad, the liner can be larger in any one or all planar dimensions than the pad (FIG. 2b). Further, either where the liners are of the same dimensions or different dimensions as the pad, the liners 61, 62 and/or 63 can have lines of weakness, such as scores or perforations 95, so as to facilitate removal of the liner from the pad (FIG. 2c).

The liner 61, 62 and/or 63 may have dimples 211 formed therein by a mechanical process which changes the conformation of the liner material such that cavities are formed in the liner which extend out of the plane 213 of the remainder of the liner material (FIG. 9). Dimples 211 in the liner may be beneficial in minimizing or preventing surface contact between selected regions of the adhesive 7 or adhesive having agent 5 applied. By minimizing the surface contact between the agent and the liner, when the liner is removed from the patch, agent is more likely to remain adhered to the patch than to adhere to the liner.

Cover

In some embodiments, the patch 11 includes a cover 117 for covering the pad 9. The cover 117, for example, can seal in the agent 5 where the agent 5 is applied to the pad upper surface 12 or where apertures 113 are formed through the thickness of the pad material 9. The cover 117 is located on the upper surface area of the pad 13, and may cover a only a portion of or the entirety of the pad upper surface area 12 (FIG. 2d). The cover 113 may be adhered to the pad upper surface 112 by a layer of adhesive 8.

Shapes

Figure 3A:
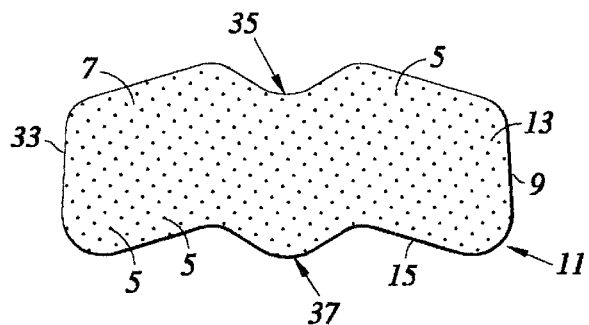
FIG. 3a is an underview of the patch showing adhesive and primary agent on an elongated, curvilinear rectangle-like shaped patch.

The patch 11 can be of different shapes and sizes for use on different locations of the skin, so as to most effectively adhere to the contours of the skin surface upon which it is used. In one embodiment, the patch comprises an elongated, curvilinear, rectangular-like shape (FIG. 3a). The patch 11 is an elongated element with end areas 33, where the peripheral edge 15 of the patch 11 defines a uniform width having an central portion with an indentation 35 on one side of the patch and a protrusion 37 on the opposite side, where the end area is approximately at least twice the area of the central portion. This shape is preferably, but not exclusively for use on the nose. The indented portion is substantially for location over the bridge 31 of the nose and the protrusion for location over the central portion of the nose 38. The end areas are substantially for location over the sides 39 of the nose as they transition towards the cheek area of the face (FIG. 4a). The agent 5 is seen applied to lines of adhesive, the agent and adhesive 7 being visible through the pad.

Figure 3B:
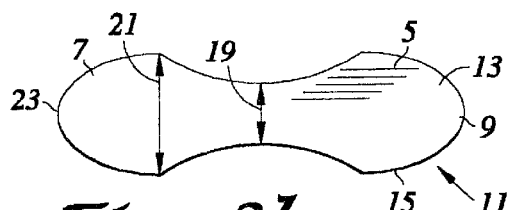
FIG. 3b is an underview of the patch showing adhesive and primary agent on an hour-glass shaped patch.

In an alternative embodiment, the patch comprises an hour-glass shape (FIG. 3b). The patch 11 is an elongated element with rounded ends 23. The peripheral edge 15 of the patch 11 defines a narrow width 19 and a broad width 21. The end area of the broad width is approximately at least twice the area of the center region having a narrow width. This shape is preferably, but not exclusively for use on the nose. The narrow width 19 is substantially for location over the bridge 31 of the nose, and the broad width 21 is substantially for location centrally over the nostril outer skin 29 (FIG. 4b). The areas leaving active agent 5 are shown as elongated lines. These lines could take different directions in different patches. There can be combinations of lines and spots as necessary.

Figure 3C:
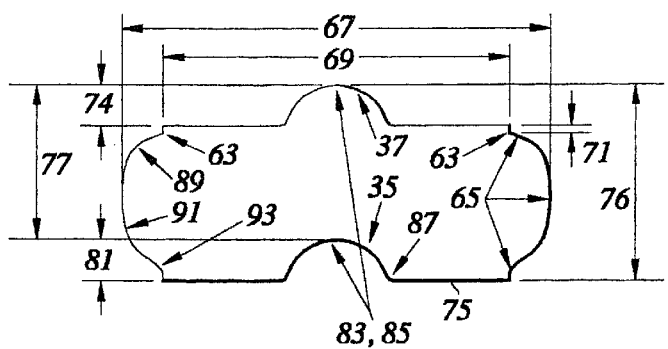
FIG. 3c is an underview of the patch of a butterfly shaped patch.

In an alternative embodiment, the patch comprises a butterfly shape (FIG. 3c). The patch 11 is an elongated element where the peripheral edge 15 of the patch 11 defines an indentation 35 on the lower side of the patch and a protrusion 37 on the upper side of the patch. There are notches 63 on the upper side of the patch. At the curvilinear end areas 65 the end areas are approximately at least twice the area of the central portion containing the indentation and protrusion.

One example of the dimensions of this embodiment include, but are not limited to the following. The total length of the patch 67 is about 3.150 inches; the length of the patch between notches 69 is about 2.3656 inches. The width of each notch 71 is about 0.0350 inches; the total width 73 of the patch from the lower side perimeter 75 to the upper most portion of the protrusion on the upper side 76 is about 1.3980 inches; the width between the upper most portion of the protrusion and the upper most portion of the indention 77 is about 1.1700 inches. The width between the upper most portion of the protrusion and the upper most portion of the notch 79 is about 0.2310 inches; the width between the upper most portion of the indention and the lower side perimeter 81 is about 0.2285 inches. The radius of curvature of the protrusion 83 and indention 85 are about 0.3128; the radius of curvature of the perimeter transition between the indention and the lower side perimeter 87 is about 0.1875. The radii of curvature of the perimeter of the curvilinear end areas are about 0.3533 89, about 0.5900 91 and about 0.3767 93, from the upper side to the lower side, respectively.

The butterfly shape is preferably, but not exclusively for use on the nose. The indented portion is substantially for location over the bridge 31 of the nose and the protrusion for location over the central portion of the nose 38, and the end areas are substantially for location over the sides 39 of the nose as they transition into the cheek area.

Figure 3D:
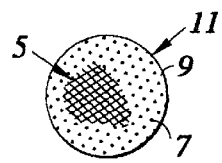
FIG. 3d is an underview of the patch showing adhesive and primary agent on a round shaped patch.

In an alternate embodiment, the patch comprises a round shape (FIG. 3d). This shape is preferably, but not exclusively for use on a small area of skin irritation, such as a single blemish (FIG. 4c). In this example the agent 5 is located on lines which cross each other. In FIG. 4c the round patch 11 includes the cover 117 over the pad 9. The agent 5 is below the cover 117. The cover may be co-extensive with the pad 9.

In further embodiments, the patch can be formed of a variety of different shapes. Examples of the shapes of the pad include, but are not limited to a triangle, square, rectangle or oval. Such shapes may be suitable for use on different regions of the face, for example the nose, forehead, cheeks, and chin.

Use of the patch, however, is not limited to the face, but rather any skin surface of the body requiring treatment. The skin is preferably in a non-hairy skin region, as the adhesive is likely to also adhere to hairs, resulting in increased pain upon removal of the patch.

Color

In some embodiments, the pad 9, adhesive 7, or both are substantially transparent, clear or colored, for instance, to conform to a flesh color or tone. In other embodiments, the upper surface of the pad 12 can be colored or rendered ornate or patterned by using different colors, patterns, shapes, words, or letters. Thus, when worn on the skin 1, there is the appearance of a colored device. The agent 5 can also be of a transparent or flesh colored nature.

Using the Carrier Patch

The method of delivering agents to the skin using the carrier patch in one preferred embodiment comprises obtaining a carrier patch, and removing the liner to expose to the skin a surface of adhesive with a primary agent. The patch with the adhesive and primary agent is applied to the skin. The lower surface of the pad adheres to the skin through the adhesive. Subsequently the patch is removed from the skin after the expiration of a given time period (FIG. 1a).

In an alternate method, the method of delivery of an agent to the skin further comprises the method of removal of keratotic plugs from the pores of the skin. This alternative method comprises obtaining a carrier patch, removing the liner to expose a surface of adhesive with agent to the skin having keratotic plugs, applying the patch with the adhesive and agent to the skin. The lower surface of the pad adheres to the skin through the adhesive. The adhesive adheres to the keratotic plugs. Subsequently the patch is removed from the skin, thereby removing keratotic plugs from the pores of the skin after the expiration of a given time period (FIG. 1b).

Although the patch is shown in use on the nose, it is clear that the patch can be used on other portions of the skin. The patch can be for use on humans and animals.

Manufacturing the Carrier Patch

The method of manufacturing for the patch 11 can be achieved, but is not limited to the method or order of operations as described below.

In one preferred embodiment, the method of manufacturing the patch 11 requires the use of a liner material 165 from roll 163. Preferably, apertures 113 are cut 99 into the first liner 61 (FIGS. 5a & 5b). Excess from liner waste materials 200 are removed from the surface of the patch at 103. The method further requires the use of a patch material 101 from roll 97, wherein the adhesive 7 is pre-adhered to the lower surface of the pad 9 material, and a waste liner 167 removed to roll 169 is pre-adhered to the adhesive.

The agent 5 is then applied to the patch lower surface at 121. The agent 5 adheres to the exposed regions of the adhesive underlying the apertures 113 in the liner 61. Excess agent remaining on the surface of the liner 61 is removed at 105. After the agent 5 is applied and adheres effectively to the adhesive 7, the first liner 61 is removed from the adhesive 7 to the waste liner roll 111. A second liner 63 can be applied to the patch from roll 125 to cover the adhesive 7 and agent 5 until the patch 11 is to be applied to the skin.

The shape of the patch 11 is kiss-cut at 107 from a ribbon 101 of pad material 9 and adhesive 7. The liner 61 may or may not be cut the same size as the pad 9. Non-adhering materials are removed as ribbons 109 of waste material onto a roll 127.

Multiple patches 11 are formed in a nested series in the manufacturing process. They are then cut and separated prior to packaging.

In another embodiment of the method, the patch material of roll 97 comprises a pad 9, adhesive 7 and first liner 61 adhered together.

In alternative embodiments of the method, apertures 113 can be cut through the lower surface 25 of the patch through the liner 61, into the adhesive 7 and/or pad 9 (FIG. 5c). Alternatively apertures 113 are can be cut from the upper surface 23 of the patch 11 through the liner into the pad 9 and/or adhesive 7 (FIG. 5d). Where apertures are cut from the upper surface of the pad 9 of the patch, a second liner may be applied to the lower surface 25 of the pad 9. Excess materials resulting from the formation of the apertures 113 are removed from the top surface 23 of the patch at 103. The agent 5 is then applied to the pad 9 at 121, such that the agent 5 is contained in the apertures 113. Excess agent 5 remaining on the pad 9 is removed at 105. Where the first agent 5 and liner were applied to the lower surface area 25 of the pad 9, the first liner 61 can be removed. A second liner 62 can be applied to cover the adhesive 7 and agent 5 until the patch is to be applied to the skin. Where the first liner 61 and agent 5 were applied to the upper surface 23 are of the pad 9, the first liner 61 can be removed, and a cover 117 can be laid upon the upper surface area 23 of the pad 9 so as to seal in the agent into the patch.

Alternative embodiments of the method of manufacturing the patch 11 require the use of an adhesive material, wherein the adhesive 7 has a first liner 61 pre-adhered to the upper surface 23 of pad 9 and a second liner 62 to the lower surface 25 of pad 9 (FIG. 5e).

Preferably, apertures 113 are cut into the first liner at 135. Excess liner materials 200 are removed from the surface of the adhesive 7 at 137. The agent 5 is then applied to the pad upper surface 23 at 139, such that the agent 5 adheres to the exposed regions of the adhesive 7 underlying the apertures 113 in the liner 61. Excess agent 5 remaining on the liner surface is removed at 141. After the agent 5 is applied and adheres effectively to the adhesive 7, the first liner 61 is removed from the patch 11 to the waste liner roll 143, and pad material can be applied to the patch from roll 145 to cover the adhesive 7 and agent 5 until the patch 11 is to be applied to the skin. In some embodiments, the primary agent 5 can be applied to the upper surface of the adhesive 7 without the use of a first liner 61.

Figure 5F:
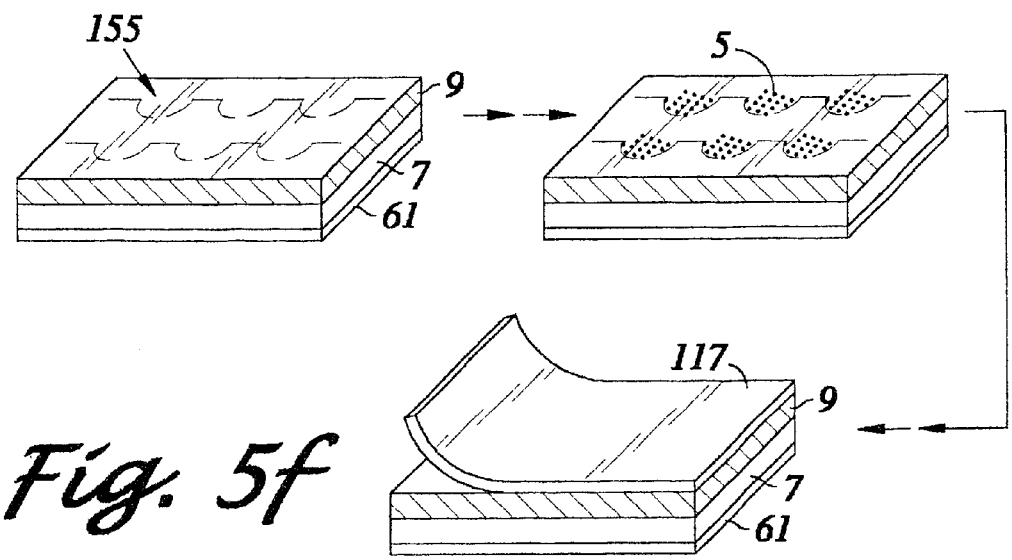
FIG. 5f is a diagrammatic view of the patch at various stages during a fifth method of manufacture.
Figure 5G:
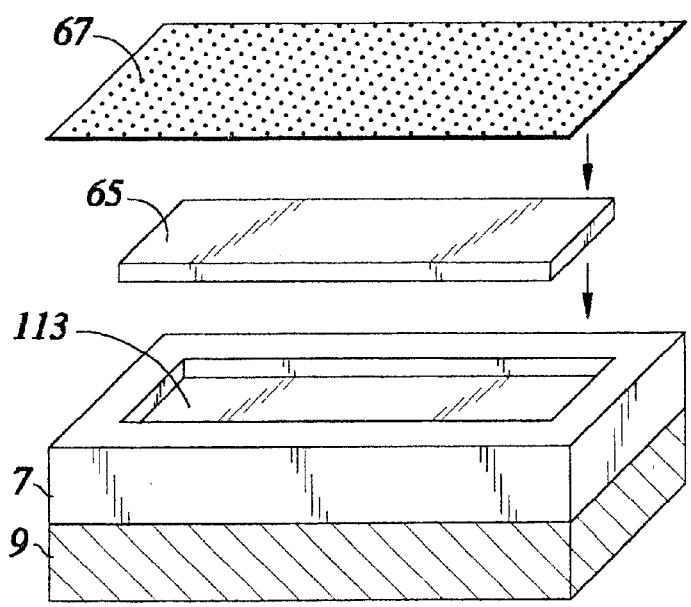
FIG. 5g is a diagrammatic view of the patch at a different stage of manufacture.

Another alternative embodiment of the method of manufacturing the patch 11 requires the use of patch material where the adhesive 7 is pre-adhered to the lower surface of the material of the pad 9, and the liner 61 is pre-adhered to the adhesive (FIG. 5f). The agent 5 can be applied to the upper surface of the pad 9. In some embodiments, the material of the pad 9 may have embossed areas to form retaining cavities 155 to hold the agent 5. Excess agent remaining on the surface of the pad 9 is removed. After the agent 5 is applied, a cover 117 can be applied to the upper surface of the patch to cover the agent 5. In some embodiments, the agent 5 can be applied to the upper surface of the pad 9 with or without the use of a cover. Alternatively, the starting patch material can comprise the pad material, and the agent 5 can be applied to the lower surface of the pad. After the agent 5 is applied, an adhesive layer 7 can be applied to the lower surface of the pad 9. Further a liner may be adhered to the adhesive layer 7 on the lower side of the patch.

Figure 6A:
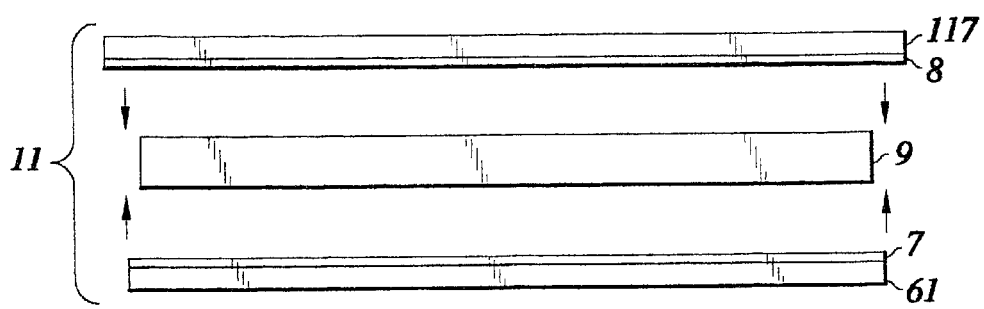
FIGS. 6a–f are cross-sectional views of carrier patches at various stages of manufacture, illustrating alternative methods of making carrier patches in accordance with the invention.
Figure 6B:
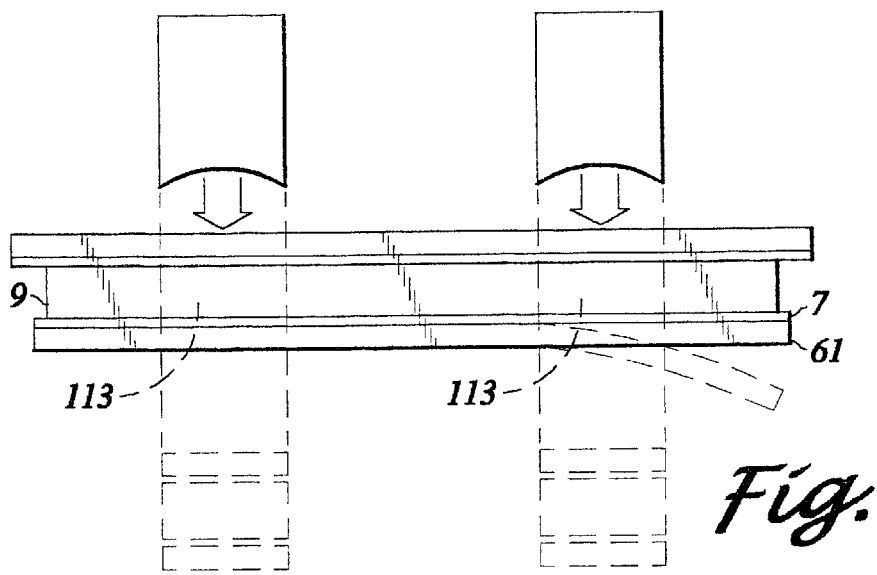
Figure 6C:
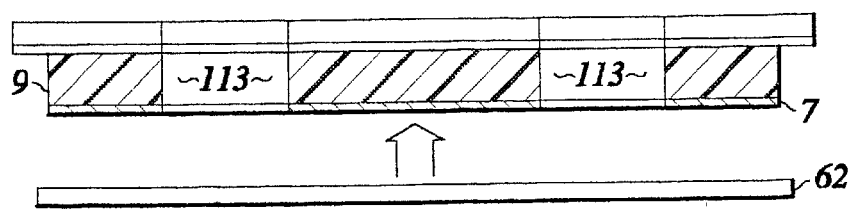

Other alternative embodiments of the method of manufacturing the carrier patch are illustrated in FIGS. 6a–f. Such methods have been described in U.S. Pat. No. 5,161,688 (Muchin). The method uses a patch 11 including a pad material 9. Adhered to the upper surface of the pad 9 is a cover material 117 and adhesive layer 8. On the lower surface there is an adhesive layer 7 and a first liner 61 covering the adhesive 7. Apertures 113 are punched through the patch material using a suitable punch or other die cutting tool well known in the art (FIG. 6b). The first liner 61 is then removed and discarded, leaving the adhesive 7 on the lower surface of the pad 9. A second liner 62 is affixed to the pad lower surface, so as to cover the apertures 113, thereby creating a plurality of retaining cavities for the agent 5. This embodiment results in no adhesive on the portion of the second liner 62 which covers the apertures (FIG. 6c).

Figure 6D:
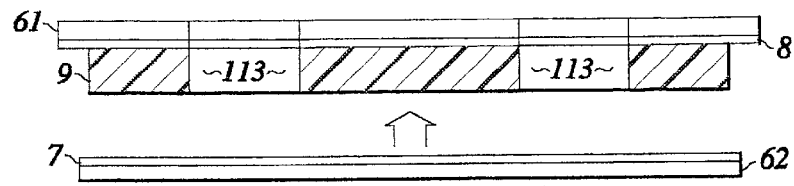
Figure 6E:
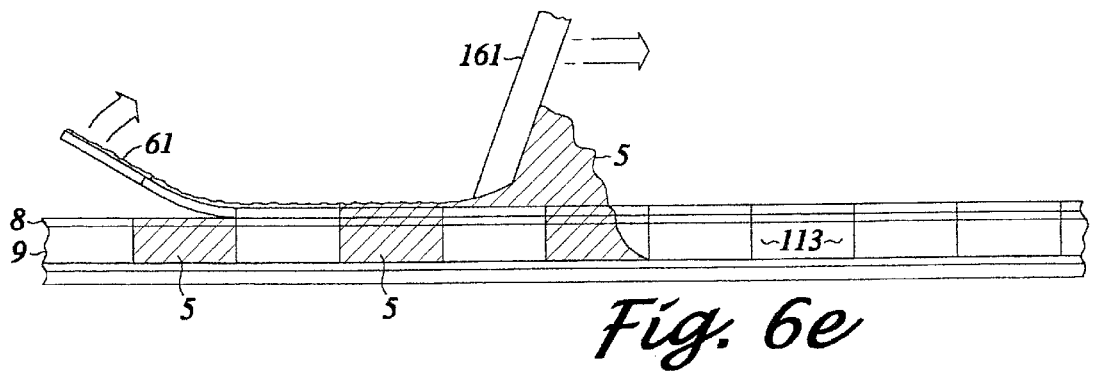
Figure 6F:
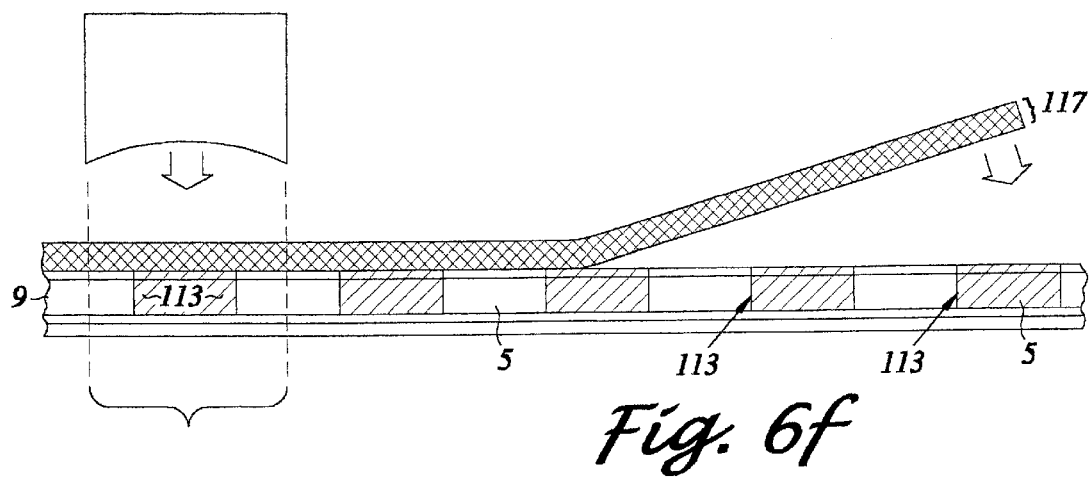

In another embodiment, the patch includes only the pad 9 and first liner 61 adhered to the upper surface of the pad by an adhesive layer 8. After apertures 113 are formed, a second liner 62 is then applied to the lower surface of the pad 9 with a layer of adhesive 7, to form a plurality of retaining cavities for the agent 5. This embodiment results in an adhesive 7 on the portion of the second liner 62 which covers the apertures (FIG. 6d). In lieu of the step of forming apertures through the patch material and the application of the first liner 61, the pad 9 can be made of an embossable material which is embossed to form the retaining cavity. An agent 5 can then be placed on the upper surface of the patch material and a knife edge or squeegee-like tool 161 used to scrape or squeegee the primary agent across the upper surface causing the primary agent to be deposited in the apertures. Other means for depositing the agent 5 in the apertures 113 may be used without departing from the invention. Once the agent 5 has been deposited into the apertures 113, the first liner 61, along with any residue on the first liner, is removed from the upper surface of the pad 9. Thus, the first liner 61 acts as a mask or protector for the remainder of the upper surface of the pad to prevent the primary agent from coming in contact with the pad or adhesive layers when the agent 5 is being squeegeed across the top surface to deposit the agent 5 in the apertures 113 (FIG. 6e).

Further, a cover 117 can be applied to the upper surface of the pad 9 to cover the apertures 113 and the agent 5 contained therein. A cutting tool 161 can be used to cut out individual patches 11.

Carrier Patch for the Delivery of Petroleum Jelly Based Agents to the Skin

In some cases, the patch may be used for the delivery of petroleum jelly based agents to the skin.

Figure 7A:
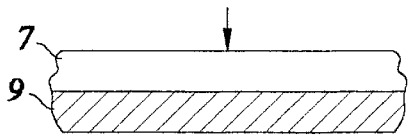
FIGS. 7a–f are diagrammatic views of one particular embodiment of the patch for the delivery of petroleum jelly based agents to the skin.
Figure 7B:
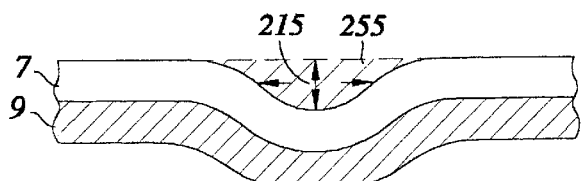
Figure 7C:
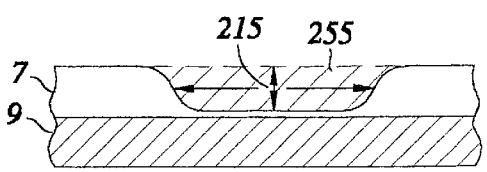
Figure 7D:
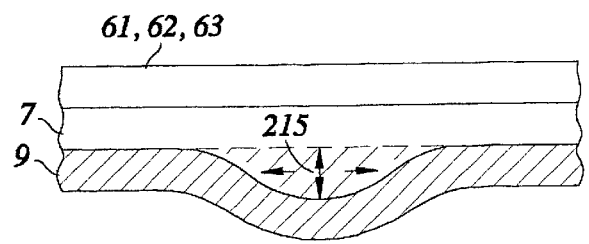
Figure 7E:
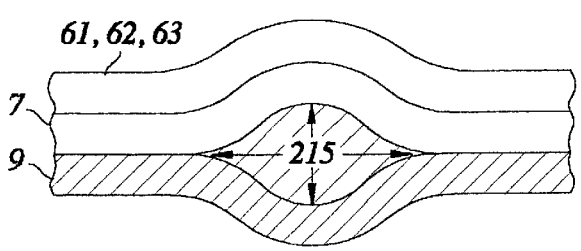
Figure 7F:
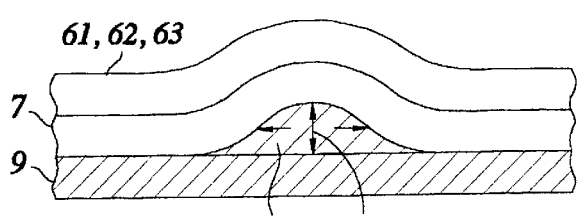

One particular embodiment of the patch useful in the delivery of a petroleum jelly based agent to the skin comprises a pad, and adhesive wherein a well 215 is formed in either the pad 9, the adhesive 7 or both, and the petroleum jelly based agent 255 is added to the well of the patch (FIGS. 7a–f). Wells, including dimples, may be formed in the patch materials by embossing, or any other means which causes a deformation in a localized area of the patch materials. This embodiment can further include a liner adhered to the adhesive lower surface. The patch may further includes a liner which may have wells 215, including dimples, formed therein (FIGS. 7d–f).

Figure 8A:
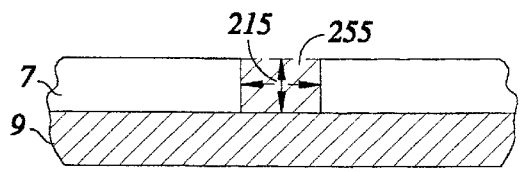
FIGS. 8a–c are diagrammatic views of a second particular embodiment of the patch for the delivery of petroleum jelly based agents to the skin.
Figure 8B:
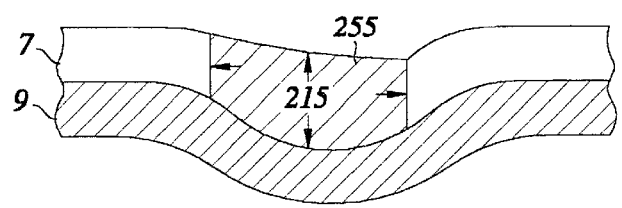
Figure 8C:
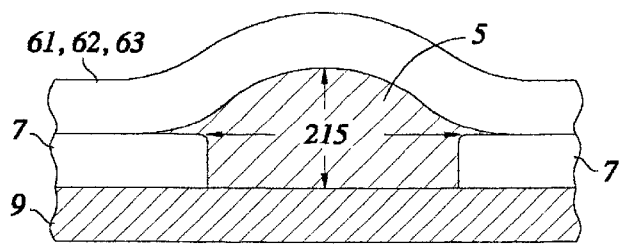

A second particular embodiment of the patch useful in the delivery of a petroleum jelly based agent to the skin comprises a pad, and adhesive wherein a well 215 is formed in either the pad 9, the adhesive 7 or both, and the petroleum jelly based agent 255 is added to the well of the patch. Wells, including dimples, may be formed in the patch materials by forming apertures in the adhesive by cutting through any portion or the entirety of the depth of the adhesive in discrete locations (FIG. 8a), leaving blank areas, areas devoid of adhesive on the lower side of the pad surface, and/or by embossing the pad and/or adhesive or effecting the patch materials in any other means which causes a deformation in a localized area of the patch materials (FIG. 8b). This embodiment can further include a liner adhered to the adhesive lower surface. The patch further includes a liner with wells 215, including dimples, formed therein. (FIG. 8c)

Figure 9A:
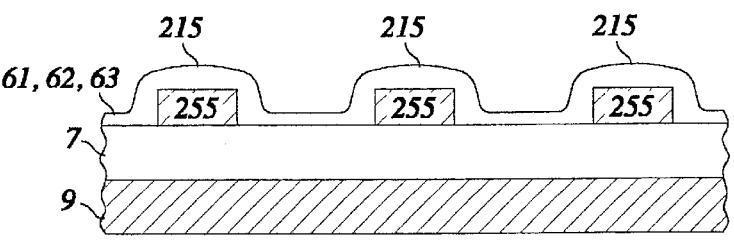
FIGS. 9a–c are diagrammatic views of a third particular embodiment of the patch for the delivery of petroleum jelly based agents to the skin.
Figure 9B:
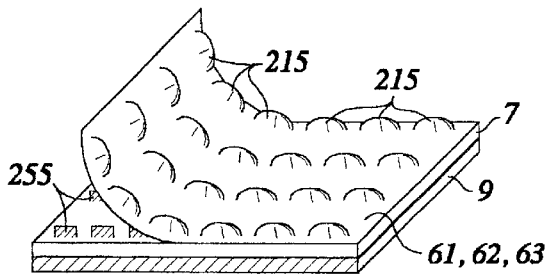
Figure 9C:
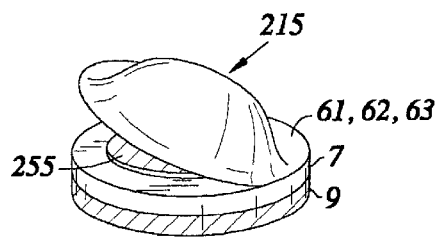

A third particular embodiment of the patch useful in the delivery of a petroleum jelly based agent to the skin comprises a pad, and adhesive, wherein the petroleum jelly based agent 255 is applied to the adhesive of the patch (FIGS. 9a–c). The patch further includes a liner with wells 215, including dimples, formed therein. Wells may be formed in the liner 61, 62 and/or 63 by any means which causes a deformation in localized areas of the liner materials. A patch may contain as few as one, but preferably several wells in the liner material of the patch.

Figure 10A:
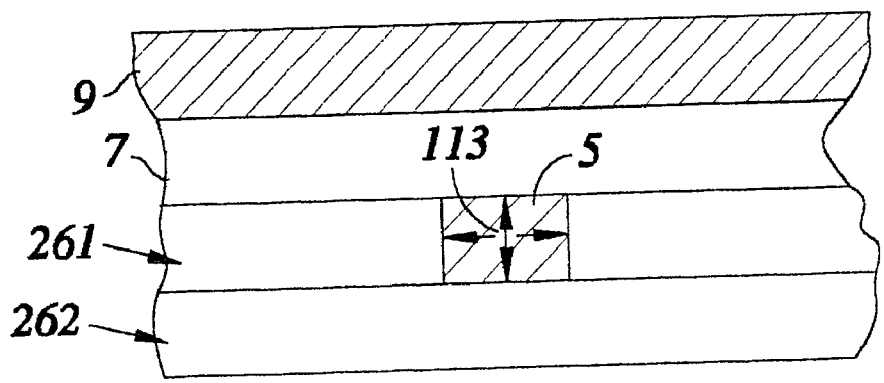
FIGS. 10a & b are diagrammatic views of a fourth particular embodiment of the patch for the delivery of agents to the skin.
Figure 10B:
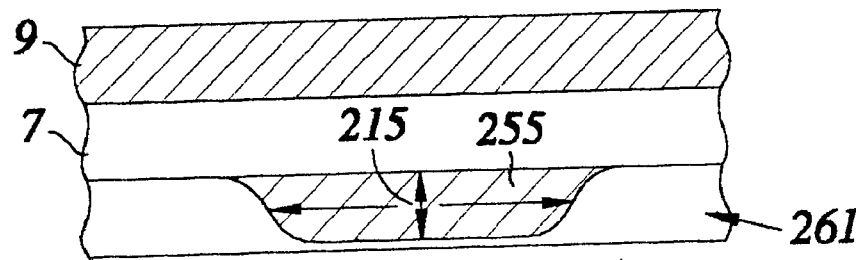

A fourth particular embodiment of the invention of the patch useful in the delivery of agents to the skin comprises a pad 9, an adhesive 7, a first liner 261 having a lower surface. In some embodiments the first liner may have apertures 113 in or a well 215 in any portion of or the entirety of the depth of the liner material. Apertures or wells are preferably filled with an agent 5 for delivery to the skin (FIGS. 10a & b).

The patch may further comprise a second liner 262 attached to the lower surface of the first liner. Where there is an aperture in the first liner, the second liner may provide a surface which encloses the aperture containing the agent (FIG. 10a). Collectively, the first and second liner form a liner layer. The liner is preferably removed by the user to expose the agent and adhesive, and to adhere the patch to the skin.

Further embodiments useful for the delivery of an agent to the skin may involve any portion of the four particular embodiments described above, as well as any variations of embodiments described throughout the application.

General

Many other forms of the invention exist, each differing from others in matters of detail only.

In some cases, the carrier patch may be used to exfoliate dead skin cells from the skin, in addition to, or in place of delivering agents to the skin. In other situations, the carrier patch may be used to exfoliate the skin in addition to delivering agents to the skin and remove keratotic plugs. Different numbers of apertures can be provided, from a simple aperture to multiple apertures. The action of the system is one where no further treatment of the adhesive is necessary which could be effectively deleterious to the operativeness of the active agent. Such treatment could be selectively mechanical, chemical or thermal.

The invention may further include any number of layers of pad material, adhesive material, liner material or cover material in any position relative to one another.

The invention may also further include any number apertures or wells in any one of, or in any combination of, either a layer of pad, adhesive or liner.

The invention is to be determined solely in terms of the following claims.

What is claimed is:

1. A carrier patch for the delivery of a petroleum jelly based primary agent to the skin, the patch having a surface area for adhering to the skin and comprising a pad having a lower surface area, an adhesive adhered to the lower surface area of the pad, said adhesive having a lower surface area and a petroleum jelly based primary agent for delivery to the skin, the petroleum jelly based primary agent having been applied to the lower surface area of the adhesive at discrete locations, and wherein the adhesive does not require a subsequent treatment which treatment could be effectively deleterious to the operativeness of the primary agent on the skin.

2. A carrier patch for the delivery of a petroleum jelly based primary agent to the skin, the patch having a surface area for adhering to the skin and comprising a pad having a lower surface area, an adhesive adhered to the lower surface area of the pad, wherein at least one well is formed in at least one of the pad or adhesive, and a petroleum jelly based primary agent for delivery to the skin, the petroleum jelly based primary agent having been applied to the wells, and wherein the adhesive does not require a subsequent treatment which treatment could be effectively deleterious to the operativeness of the primary agent on the skin.

3. A carrier patch for the delivery of petroleum jelly based primary agent to the skin, the patch having a surface area for adhering to the sin and comprising a pad having a lower surface area, an adhesive adhered to the lower surface area of the pad, and a first liner adhered to the patch by the adhesive, the first liner defining a depth and at least one aperture in the liner, the aperture extending substantially through the entirety of the depth of the liner, wherein the liner forms a mask effect such that discrete areas of adhesive are exposed, and petroleum jelly based primary agent for delivery to the skin, the petroleum jelly based primary agent having been applied to the aperture of the liner, and wherein the adhesive does not require a subsequent treatment which treatment could be effectively deleterious to the operativeness of the primary agent on the skin.

4. The carrier patch as claimed in claim 1 or 2 further comprising a first liner adhered to the adhesive, the first liner being removable.

5. The carrier patch as claimed in claim 4, wherein the first liner has at least one well formed therein, and wherein the well defines selectively an aperture through which the primary agent is applied to the adhesive.

6. The carrier patch as claimed in claim 5, wherein the first liner has at least one dimple formed therein.

7. The carrier patch as claimed in any one of claims 1, 2 or 3 further comprising a second liner adhered to the adhesive.

8. The carrier patch as claimed in claim 7, wherein the second liner has at least one dimple formed therein.

9. The carrier patch as claimed in any one of claims 1, 2 or 3, wherein the deleterious treatment is at least one of a chemical, thermal or mechanical action.

10. The carrier patch as claimed in any one of claims 1, 2 or 3, wherein the adhesive requires premoisturization prior to application to the skin.

11. The carrier patch as claimed in any one of claims 1, 2 or 3, wherein the adhesive does not require premoisturization prior to application to the skin.

12. The carrier patch as claimed in any one of claims 1, 2 or 3, wherein the adhesive includes a polymeric adhesive composition.

13. The carrier patch as claimed in any one of claims 1, 2 or 3, wherein the Adhesive includes a pressure sensitive adhesive.

14. The carrier patch as claimed in any one of claims 1, 2 or 3, wherein the pressure sensitive adhesive comprises an acrylate adhesive.

15. The carrier patch as claimed in any one of claims 1, 2 or 3, wherein the primary agent is therapeutic.

16. The carrier patch as claimed in any one of claims 1, 2 or 3, wherein the adhesive of the carrier patch is active in the physical removal of keratotic plugs from the skin, the keratotic plug including dead epidermal cells formed within skin pores.

17. The carrier patch as claimed in any one of claims 1, 2 or 3, wherein the primary agent is distributed at least across a portion of the surface area of the patch.

18. The carrier patch as claimed in any one of claims 1, 2 or 3, wherein the primary agent is distributed over entirety of the surface area of the patch.

19. The carrier patch as claimed in any one of claims 1, 2 or 3, where the pad is formed by at least one of a cotton cloth, rayon cloth, tetron cloth, nylon cloth or plastic film.

20. The carrier patch as claimed in any one of claims 1, 2 or 3, where the pad is material has embossed areas to form retaining cavities.

21. The carrier patch as claimed in any one of claims 1, 2 or 3, where the adhesive includes at least one of a solvent, pigment or oil.

22. The carrier patch as claimed in any one of claims 1, 2 or 3, wherein the pad or adhesive further includes a secondary agent.

23. The carrier patch as claimed in any one of claims 1, 2 or 3, wherein the patch includes a cover adhered to the upper surface area of the pad, and wherein the cover is on an opposite side of the adhesive.

24. The carrier patch as claimed in any of claims 1, 2 or 3 wherein the petroleum jelly based primary agent includes at least one of polymyxin B sulfate or bacitracin zinc.

25. The carrier patch as claimed in claim 24 wherein the petroleum jelly based primary agent further includes neomycin sulfate.

* * * * *